(12) United States Patent
McCarthy et al.

(10) Patent No.: US 10,702,163 B2
(45) Date of Patent: Jul. 7, 2020

(54) SYSTEMS AND METHODS FOR INTRACAVITARY TEMPERATURE MEASUREMENT AND MONITORING

(71) Applicant: Precision EP GmbH, Dresden (DE)

(72) Inventors: John McCarthy, Newbury, NH (US); Martin Matthes, Heidenau (DE); Tim Lenihan, Hradec Kralove (CZ); Wenzel F. Hurtak, Cogolin (FR)

(73) Assignee: Precision EP GmbH, Dresden (DE)

( * ) Notice: Subject to any disclaimer, the term of this patent is extended or adjusted under 35 U.S.C. 154(b) by 497 days.

(21) Appl. No.: 15/583,798

(22) Filed: May 1, 2017

(65) Prior Publication Data

US 2017/0319076 A1 Nov. 9, 2017

Related U.S. Application Data

(60) Provisional application No. 62/331,362, filed on May 3, 2016.

(51) Int. Cl.
*A61B 5/00* (2006.01)
*A61B 5/01* (2006.01)

(52) U.S. Cl.
CPC ............ *A61B 5/0086* (2013.01); *A61B 5/002* (2013.01); *A61B 5/0008* (2013.01);
(Continued)

(58) Field of Classification Search
CPC ....... A61B 5/0086; A61B 5/0008; A61B 5/01; A61B 5/4233; A61B 5/002; A61B 5/0022;
(Continued)

(56) References Cited

U.S. PATENT DOCUMENTS

| 5,433,216 A | 7/1995 | Sugrue et al. |
| 5,792,070 A | 8/1998 | Kauphusman et al. |

(Continued)

FOREIGN PATENT DOCUMENTS

| EP | 0 856 278 A2 | 8/1998 |
| EP | 2 642 913 A2 | 10/2013 |
| EP | 2 716 323 A1 | 4/2014 |

OTHER PUBLICATIONS

Badger, et al., Initial experience of assessing esophageal tissue injury and recovery using delayed-enhancement MRI after atrial fibrillation ablation, Circ. Arrhythm Electrophysiol, 2:620-5 (2009).

(Continued)

*Primary Examiner* — Theodore J Stigell
*Assistant Examiner* — Amy J Shafqat
(74) *Attorney, Agent, or Firm* — Eversheds Sutherland (US) LLP; Christopher C. Bolten; Nicola A. Pisano

(57) ABSTRACT

Systems and methods for measuring and monitoring intracavitary tissue temperature. The system may include a catheter shaft with a circuit board disposed therein, the circuit board having an array of sensors disposed thereon. The catheter shaft may have an opening and an expandable structure surrounding the opening to provide a field of view of the intracavitary tissue for the array of sensors through the opening. The system may include a software-based programming system run on a computer such that a clinician may review information indicative of temperature of the intracavitary tissue, and be alerted if the temperature exceeds a predetermined threshold.

20 Claims, 9 Drawing Sheets

(52) U.S. Cl.
CPC .............. *A61B 5/0022* (2013.01); *A61B 5/01* (2013.01); *A61B 5/4233* (2013.01); *A61B 5/6853* (2013.01); *A61B 5/7225* (2013.01); *A61B 5/746* (2013.01); *A61B 5/7475* (2013.01); *A61B 5/0031* (2013.01); *A61B 5/6859* (2013.01); *A61B 2562/0271* (2013.01); *A61B 2562/043* (2013.01); *A61B 2562/166* (2013.01)

(58) Field of Classification Search
CPC ... A61B 5/7475; A61B 5/6853; A61B 5/7225; A61B 5/746; A61B 2562/166; A61B 2562/0271; A61B 5/0031; A61B 5/6859; A61B 2562/043
See application file for complete search history.

(56) References Cited

U.S. PATENT DOCUMENTS

| | | | |
|---|---|---|---|
| 8,187,221 | B2 | 5/2012 | Bates |
| 2003/0233052 | A1* | 12/2003 | Kokate ............... A61B 5/015 600/549 |
| 2003/0236443 | A1* | 12/2003 | Cespedes ............ A61B 5/01 600/29 |
| 2004/0204651 | A1* | 10/2004 | Freeman ........... A61B 5/0075 600/473 |
| 2007/0239062 | A1* | 10/2007 | Chopra ............... A61B 5/01 600/549 |
| 2009/0264727 | A1 | 10/2009 | Markowitz et al. |
| 2011/0066035 | A1 | 3/2011 | Norris et al. |
| 2014/0012155 | A1 | 1/2014 | Flaherty et al. |
| 2014/0206973 | A1* | 7/2014 | Kassab ............... A61B 5/0031 600/375 |
| 2016/0206373 | A1* | 7/2016 | Chen .................. A61B 5/0084 |
| 2017/0143214 | A1* | 5/2017 | Garibotto ........... A61B 5/6852 |
| 2017/0156793 | A1* | 6/2017 | Melsky .............. A61B 18/22 |

OTHER PUBLICATIONS

Bahnson, TD., Strategies to minimize the risk of esophageal injury during catheter ablation for atrial fibrillation, Pacing Clin. Electrophysiol, 32:248-60 (2009).

Cummings, et al., Brief Communication: Atrial-Esophageal Fistulas After Radiofrequency Ablation, Ann. Intern. Med., 144:572-574 (2006).

Doll, et al., Esophageal Perforation During Left Atrial Radio-Frequency Ablation: is the risk too high? J. Thorac. Cardiovasc. Surg, 125:836-842 (2003).

Gilcrease, et al., A Delayed Case of Fatal Atrioesophageal Fistula following Radiofrequency Ablation for Atrial Fibrillation, J. Cardiovasc. Electrophysiol, 21(6):708-711 (2010).

Gillinov, et al., Esophageal injury during radio-frequency ablation for atrial fibrillation, J. Thorac. Cardiovasc. Surg., 122:1239-1240 (2001).

Go, et al., Prevalence of Diagnosed Atrial Fibrillation in Adults: National Implications for Rhythm Management and Stroke Prevention: the AnTigoagulation and Risk Factors in Atrial Fibrillation (ATRIA) Study, JAMA, 285:2370-2375 (2001).

Haissaguerre, et al., Spontaneous initiation of atrial fibrillation by ectopic beats originating in the pulmonary veins, N. Engl. J. Med., 339:659-666 (1998).

Lemola, et al., Computed tomographic analysis of the anatomy of the left atrium and the esophagus: implications for left atrial catheter ablation, Circulation, 110:3655-60 (2004).

Lin, et al., Catheter Ablation of Paroxysmal Atrial Fibrillation Initiated by Non-Pulmonary Vein Ectopy, Circulation, 107:3176-3183 (2003).

Marrouche, et al., Circular mapping and ablation of the pulmonary vein for treatment of atrial fibrillation: impact of different catheter technologies, J. Am. Coll. Cardiol., 40:464-474 (2002).

Meng, et al., Late gadolinium enhancement of the esophagus is common on cardiac MR several months after pulmonary vein isolation: preliminary observations, Pacing Clin. Electrophysiol,33:661-6 (2010).

Muller, et al., Higher incidence of esophageal lesions after ablation of atrial fibrillation related to the use of esophageal temperature probes, Heart Rhythm, 12(7):1464-1469 (2015).

Nguyen, et al., Effect of radiofrequency energy delivery in proximity to metallic medical device components, Heart Rhythm, 12(10):2162-2168 (2015).

Oral, et al., Catheter Ablation for Paroxysmal Atrial Fibrillation: Segmental Pulmonary Vein Ostial Ablation Versus Left Atrial Ablation, Circulation, 108:2355-2360 (2003).

Pappone, et al., Atrial Electroanatomic Remodeling After Circumferential Radiofrequency Pulmonary Vein Ablation: Efficacy of an Anatomic Approach in a Large Cohort of Patients With Atrial Fibrillation, Circulation, 104:2539-2544 (2001).

Pappone, et al., Atrio-Esophageal Fistula as a Complication of Percutaneous Transcatheter Ablation of Atrial Fibrillation, Circulation, 109:2724-2726 (2004).

Pappone, et al., Prevention of iatrogenic atrial tachycardia after ablation of atrial fibrillation: a prospective randomized study comparing circumferential pulmonary vein ablation with a modified approach, Circulation, 110:3036-3042 (2004).

Perzanowski, et al., Real-time monitoring of luminal esophageal temperature during left atrial radiofrequency catheter ablation for atrial fibrillation: observations about esophageal heating during ablation at the pulmonary vein Ostia and posterior left atrium, J. Cardiovasc. Electropysiol, 17:166-70 (2006).

Redfearn, et al., Esophageal temperature monitoring during radiofrequency ablation of atrial fibrillation, J. Cardiovas. Eletrophysiol, 16:589-93 (2005).

Ren, et al., Utility of intracardiac echocardiography in left heart ablation for tachyarrhythmias, Echocardiography, 24:533-40 (2007).

Scanavacca, et al., Left atria-esophageal fistula following radiofrequency catheter ablation of atrial fibrillation, J. Cardiovas. Electro-physiol., 15:960-962 (2004).

Teplitsky, et al., Radiofrequency catheter ablation for atrial fibrillation produces delayed and long lasting elevation of luminal esophageal temperature independent of lesion duration and power, Heart Rhythm, 2(5):S8-S9 (2005).

www.circascientific.com/products/circa-s-cath-us, Circa's S-Cath™ Hot & Cold Esophageal Temperature Monitoring System, Circa S-Cath™ Esophageal Temperature Probe, 6 pages, retrieved, May 3, 2017.

www.circascientific.com/technology-6, Circa, retrieved May 3, 2017, 3 pages.

www.fiab.it/en/prodotti.php?id-162, Esophageal Temperature Monitoring System, Esotest Monitor & Esotest Probe, retrieved May 3, 2017, 1 page.

International Search Report and Written Opinion dated Jul. 26, 2017 in Int'l PCT Patent Appl. Serial No. PCT/IB2017/052528.

* cited by examiner

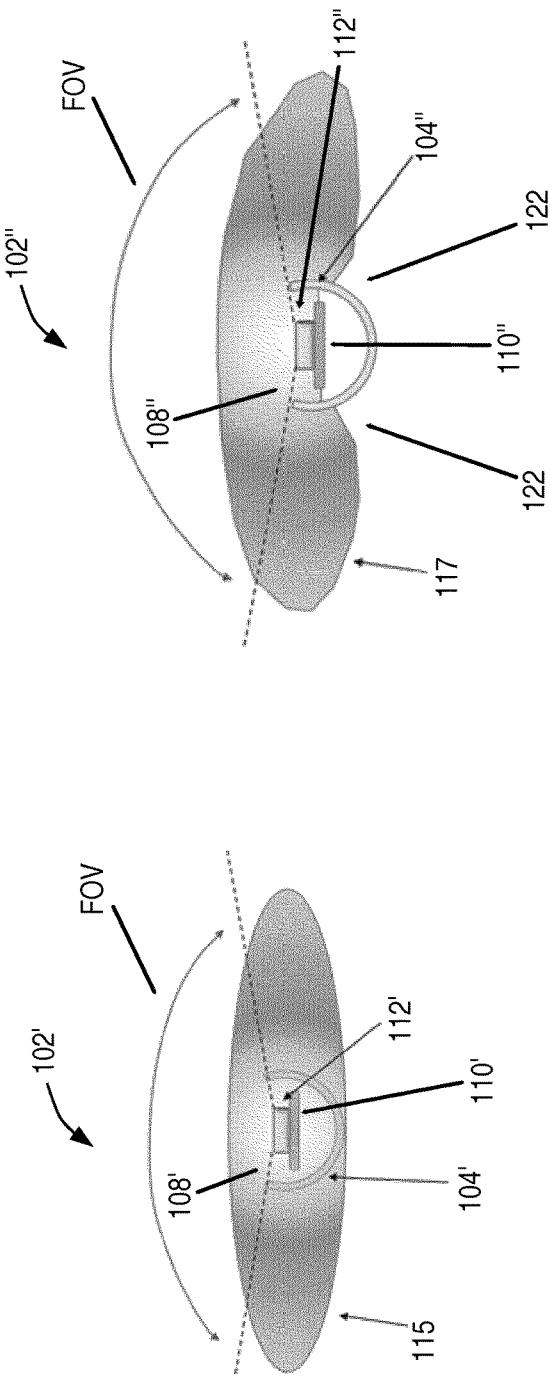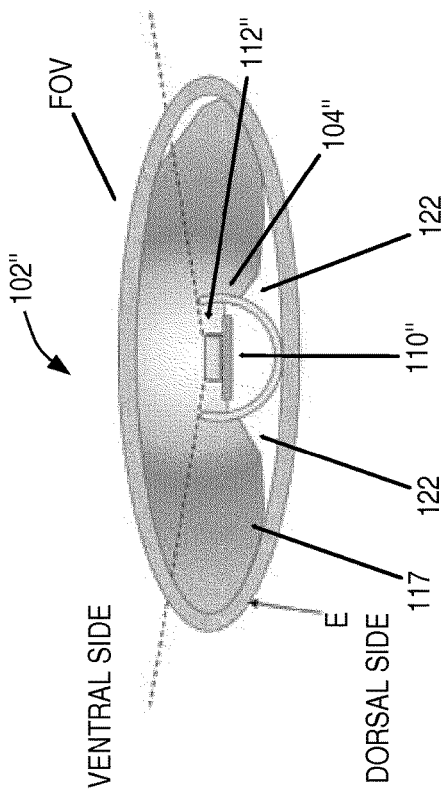

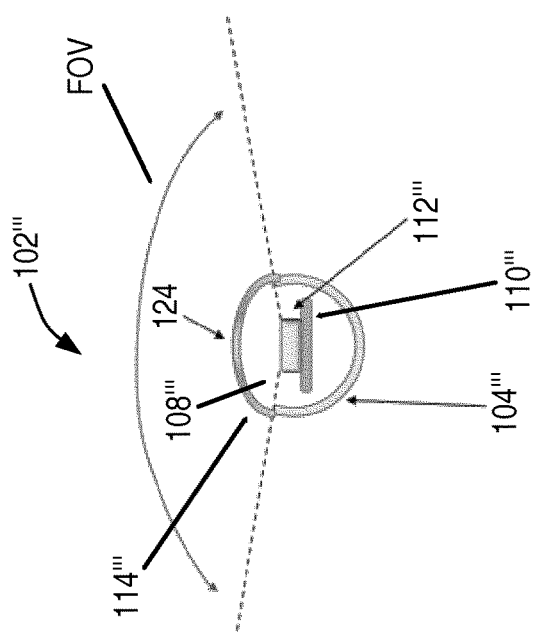
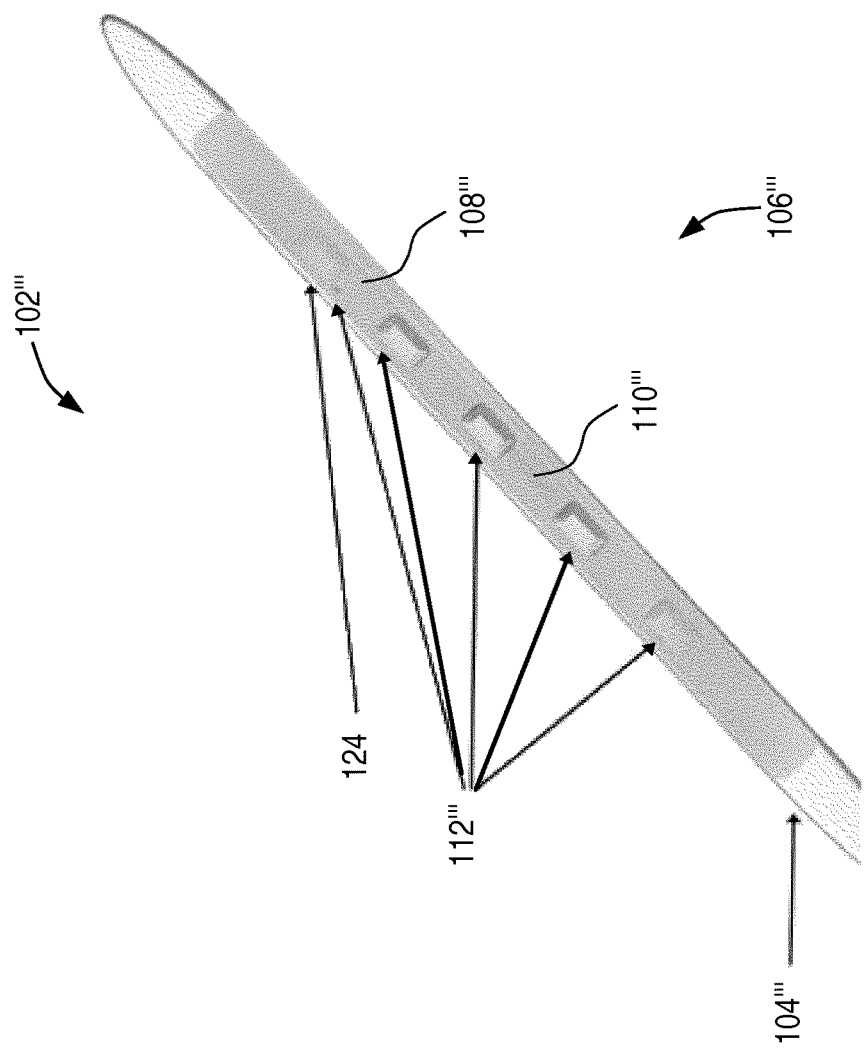
FIG. 4B
FIG. 4A

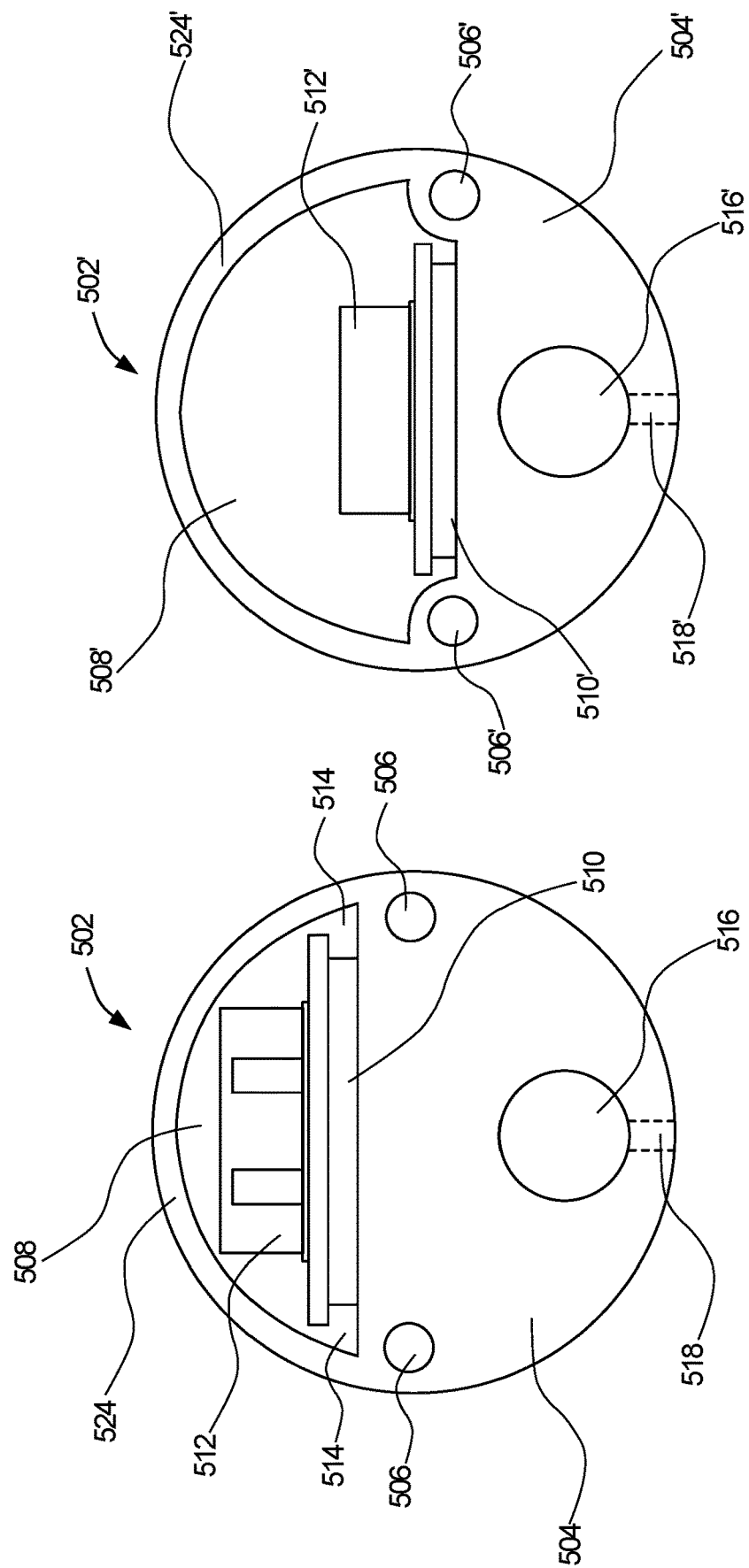

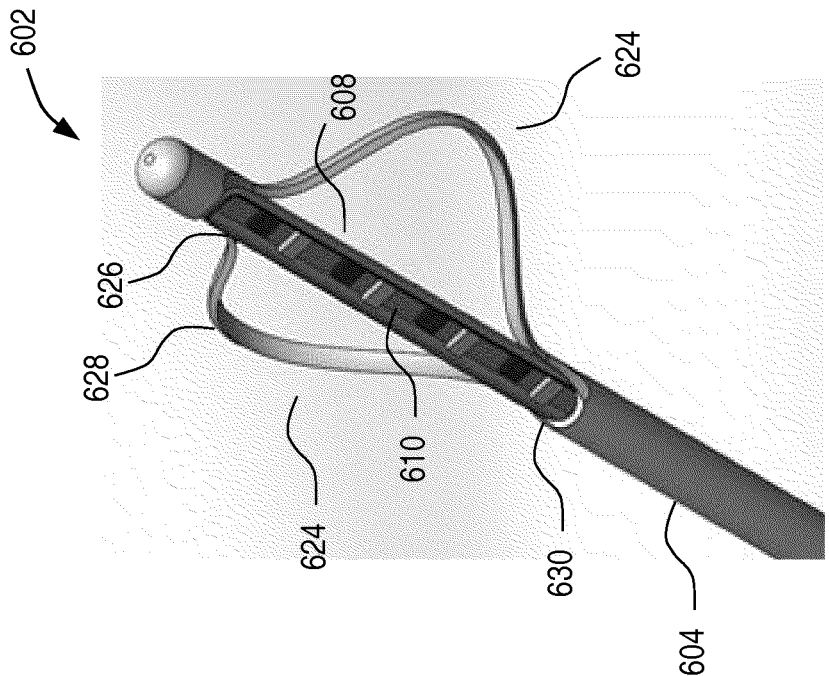
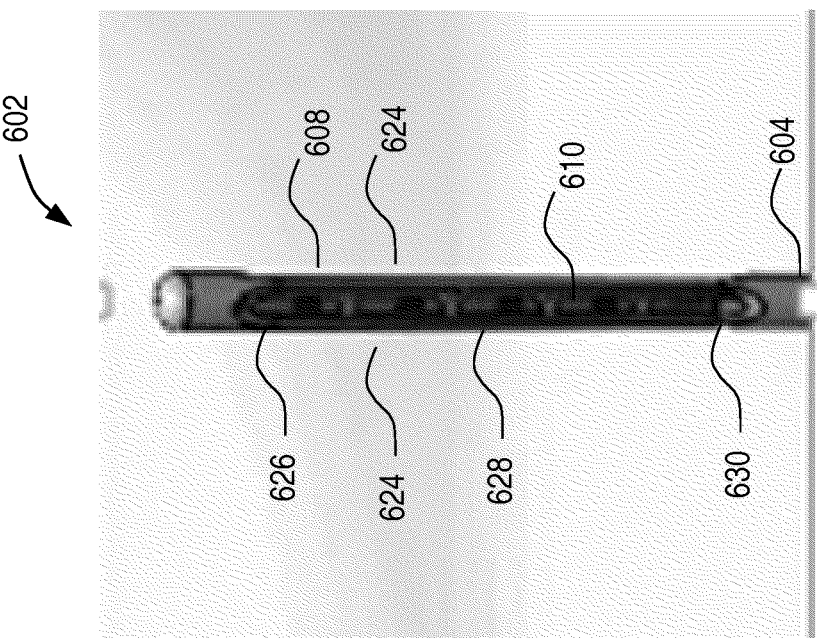
FIG. 6B
FIG. 6A

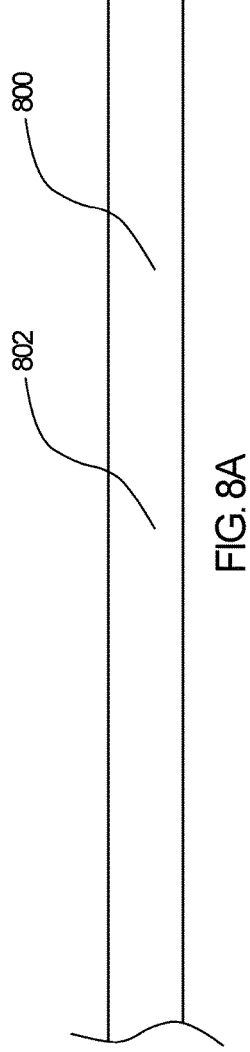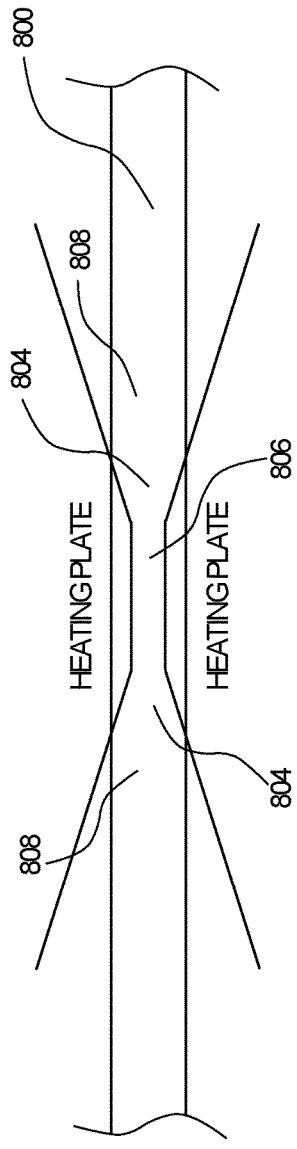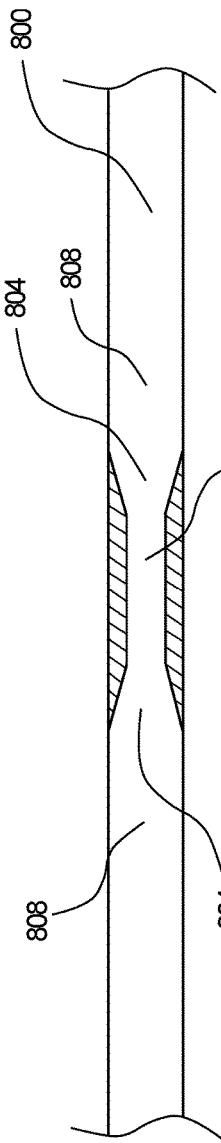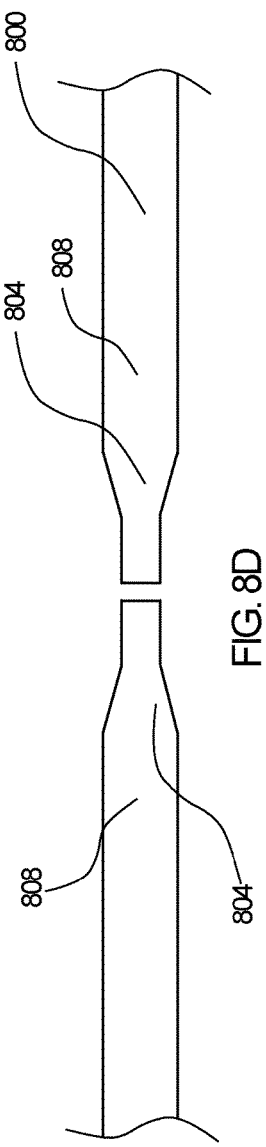

SYSTEMS AND METHODS FOR INTRACAVITARY TEMPERATURE MEASUREMENT AND MONITORING

CROSS-REFERENCE TO RELATED APPLICATION

This application claims priority to U.S. Provisional Patent Application No. 62/331,362, filed on May 3, 2016, the entire contents of which are incorporated herein by reference.

FIELD OF USE

This application generally relates to systems and methods for measurement and monitoring intracavitary tissue temperature.

BACKGROUND

Atrial fibrillation (AF) is a major cause of stroke and the most common arrhythmia that is clinically significant, with prevalence rates of 3.8% in individuals 60 years of age or older and 9.0% in individuals over 80 years of age. In 2001, the prevalence of AF was projected to increase 2.5-fold by 2050 due to the rapidly growing elderly population. One surgical treatment method for AF is called the maze procedure, which was developed in 1991 by Cox. In this procedure, incisions are made directly into the atrium of the heart during major, open heart surgery. While successful, due to the procedure's long operative time and morbidity rate, most clinicians have adopted a variation of the procedure which uses percutaneous radiofrequency ablation (RFA) to create transmural lines of electrically inactive scar tissue within the left atrium (LA), endocardially. As a result, there has been an increase in RFA techniques to treat paroxysmal and persistent atrial fibrillation. The approach to RFA changed dramatically in 1998 with the discovery by Haïssaguerre and associates that the majority of ectopic atrial beats originated somewhere within 1 or more of the 4 pulmonary veins (PVs) due to the extension of muscular bands from the LA into the PVs. Following this discovery, mapping and ablation of arrhythmogenic foci of both the PVs and the LA have been performed, with today's procedures showing success rates of 60-90%.

Although RFA has been effective at treating atrial fibrillation, complications have been reported, the most serious of which is a left atrial-esophageal fistula that forms secondary to thermal esophageal injury. Atrio-esophageal fistula is the most dreadful and lethal complication among all others related to AF catheter ablation. Patients with an atrio-esophageal fistula may be presented with a variety of signs and symptoms such as chest pain, heartburn, dysphagia, anorexia, and hematemesis immediately after or also late after the index procedure. Usually death occurs because of cerebral or myocardial air embolism, endocarditis, massive gastrointestinal bleeding and septic shock. New esophageal late gadolinium enhancement has been shown to be present in almost one-third of patients after AF ablation, suggesting some form of esophageal injury. This finding is irrespective of the type of catheter ablation (irrigated vs. not-irrigated tip) used during the procedure, of ablation time, of anatomical location of the esophagus compared with the left atrium, of the size of left atrium cavity or of the timing of cardiac magnetic resonance study after pulmonary vein isolation.

As demonstrated by computed tomography, cardiac magnetic resonance, and intracardiac echocardiography, the strict anatomic relationship between the left atrium and the esophagus together with the delivery of radiofrequency energy on the posterior wall of the left atrium are the principal causes leading to the occurrence of atrio-esophageal fistula or, more generally, of esophageal injury.

Since radiofrequency energy exerts a rise in local temperatures, it is common practice now to monitor the esophageal temperature with an esophageal probe to titrate the radiofrequency energy application on the areas at potential risk of esophageal injury and to stop radiofrequency energy delivery when a rapid elevation of the esophageal internal temperature is recorded. However, a problem with current systems and methods for measuring and monitoring intracavitary tissue temperature is poor correlation between esophageal internal temperature and total radiofrequency energy delivery.

For example, in U.S. Patent Pub. No. 2014/0012155 to Flaherty, a device having a plurality of sensors is used to monitor temperature of esophageal tissue while actively ablating target tissue to reduce risk of injury to untargeted tissues. The device may be positioned within the esophagus with positioning elements. However, the accuracy of esophageal temperature monitoring to estimate the esophageal heating and then anticipating the formation of the esophageal injury is uncertain. For example, particles, fluids and gases traversing the esophagus may obstruct the field of view of the sensors, resulting in inaccurate temperature measurements.

It would therefore be desirable to provide improved systems and methods for measuring and monitoring intracavitary tissue temperature.

Specifically, it would be desirable to provide systems and methods for measuring and monitoring intracavitary tissue temperature using a device tailored for optimal introduction to, positioning at, and having an optimum, unobstructed field of view of, the target tissue.

SUMMARY

The present invention overcomes the drawbacks of previously-known systems by providing systems and methods for measuring and monitoring intracavitary tissue temperature using a device having an expandable structure that provides optimal field of view of the target tissue, resulting in accurate and early indicators of tissue injury. For example, the intracavity tissue may be tissue at the inner wall of a body lumen such as the esophagus so that the systems and methods permit measuring and monitoring tissue temperature at the inner wall of the body lumen.

In accordance with one aspect of the present invention, a system for intracavitary tissue temperature measurement and monitoring is provided. The system may include an introducer device sized and shaped to be positioned adjacent to an intracavitary tissue and software that runs on a computer operatively coupled to the introducer device.

The introducer device may include a catheter shaft having a distal end, a longitudinal axis, a lumen extending therethrough, and an opening at the distal end along the longitudinal axis such that at least a portion of the lumen is exposed. The catheter shaft may have a circuit board at least partially disposed in the opening at the distal end of the catheter shaft, wherein the circuit board has an array of infrared sensors disposed thereon. The circuit board may be rotated within the catheter shaft to alter a field of view through the opening of the catheter shaft. The sensors of the array of infrared sensors may each have circuitry integrate therewith that is programmed to generate a signal indicative of temperature of the intracavitary tissue.

The introducer device may also include an expandable structure formed from an infrared transmissive material and disposed on the catheter shaft proximal to the opening at the distal end to surround the array of infrared sensors, providing a field of view through the opening. The expandable structure may be a restrained or unrestrained inflatable bladder providing an optimum viewing distance between the array of infrared sensors and the intracavitary tissue. Alternatively, the introducer device may have a transmissive foil glued or sealed to the edges of the opening of the catheter shaft, thereby providing the array of infrared sensors a field of view through the opening.

The non-transitory computer readable media has instructions stored thereon that, when executed by a processor operatively coupled to the circuit board, cause a graphical user interface to display information indicative of temperature of the intracavitary tissue based on the signal from the array of infrared sensors. The instructions stored on the non-transitory computer readable media may also cause, when executed by the processor, the graphical user interface to trigger an alarm if the generated signal indicative of temperature of the intracavitary tissue exceeds a predetermined threshold to alert the patient's clinician. Accordingly, the clinician may cease or adjust the application of RF ablation to nearby tissue to thereby prevent esophageal injury.

In accordance with another aspect of the present invention, a method for measuring and monitoring intracavitary tissue temperature using the system described above is provided. First, the clinician positions the introducer device adjacent to an intracavitary tissue such that the opening of the catheter shaft is oriented toward the intracavitary tissue. The clinician then inflates the bladder to provide a field of view through the opening and an optimal viewing distance between the array of infrared sensors and the intracavitary tissue. The clinician optionally may rotate, either manually or by a motor, the circuit board within the lumen of the catheter shaft to achieve a desired field of view of the intracavitary tissue.

Next, the clinician instructs the array of infrared sensors to detect infrared radiation emitted by the intracavitary tissue. The circuitry integrated with each sensor of the array of infrared sensors then processes the detected infrared radiation to generate a signal indicative of temperature of the intracavitary tissue. Processing the detected infrared radiation may include amplifying the signal, filtering the signal, performing compensation for local actual temperature of the one or more infrared sensors, and converting the signal to a digital serial stream for convenient use by the clinician's computer.

Finally, the processed information indicative of temperature of the intracavitary tissue based on the generated signal is displayed on a graphical user interface. In addition, the graphical user interface may trigger an alarm if the generated signal indicative of temperature of the intracavitary tissue exceeds a predetermined threshold to alert the clinician so that the clinician may cease or adjust the application of RF ablation to nearby tissue to thereby prevent esophageal injury.

BRIEF DESCRIPTION OF THE DRAWINGS

FIG. 3A shows a front cross-sectional view of an alternative embodiment of the introducer device of FIG. 1A.

FIG. 3B shows a front cross-sectional view of an alternative embodiment of the introducer device of FIG. 3A having a restrained bladder element.

FIG. 3C shows a front cross-sectional view of the introducer device of FIG. 3B disposed within an esophagus.

FIGS. 4A and 4B show an alternative embodiment of the introducer device of FIG. 1A, where FIG. 4A is a schematic view and FIG. 4B shows a front cross-sectional view of the alternative embodiment of the introducer device.

FIG. 5A shows an alternative embodiment of the introducer device of FIG. 4A. FIG. 5B shows an alternative embodiment of the introducer device of FIG. 5A.

FIGS. 6A and 6B show an alternative embodiment of the introducer device in accordance with the principles of the present invention, where the introducer device is in a delivery state in FIG. 6A and in a deployed state in FIG. 6B.

FIGS. 8A to 8D illustrate an exemplary method for manufacturing the expandable structure of FIG. 1A.

DETAILED DESCRIPTION

The systems and methods of the present invention may provide accurate measuring and monitoring of intracavitary tissue temperature by providing an optimal field of view over a large surface area of the intracavitary tissue. In accordance with the principles of the present invention, the systems and methods may be optimized for use in the esophagus to measure and monitor esophageal tissue to effectively prevent esophageal injury and atrio-esophageal fistula.

Figure 1A:
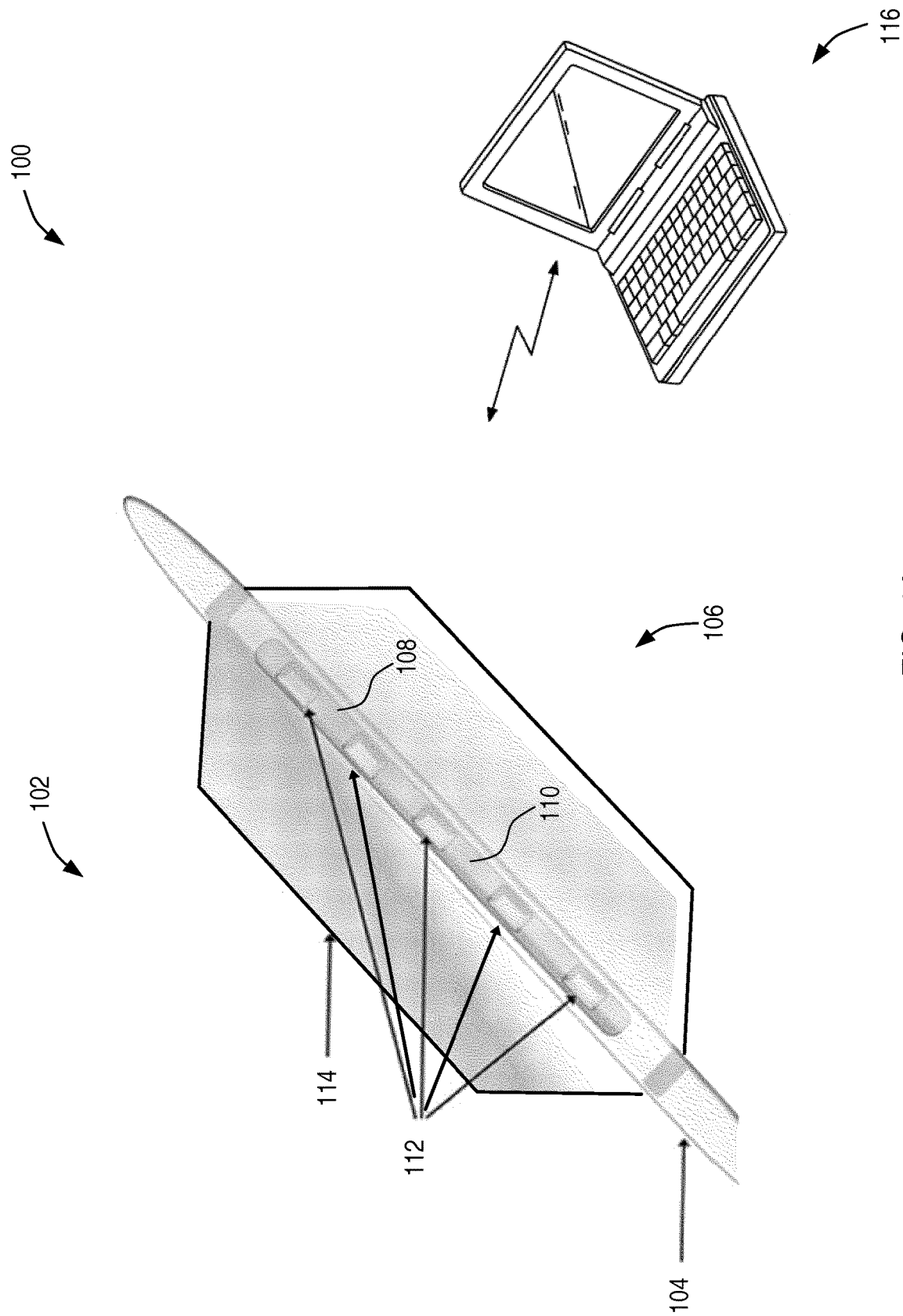
FIG. 1A is a schematic view of an exemplary embodiment of a system constructed in accordance with the principles of the present invention.

Referring to FIG. 1A, an overview of intracavitary probe system 100 in accordance with one embodiment of the present invention is provided. In FIG. 1A, components of the system are not depicted to scale on either a relative or absolute basis. Intracavitary probe system 100 comprises introducer device 102 and software-based monitoring system 116.

In the illustrated embodiment, introducer device 102 includes catheter shaft 104, circuit board 110, and expandable structure 114. Catheter shaft 104 has distal end 106 adapted to be inserted in a body lumen, e.g., the esophagus, adjacent to an intracavitary tissue, e.g., wall of body lumen cavity. Catheter shaft 108 also has a lumen extending therethrough for receiving circuit board 110. Catheter shaft 104 may include opening 108 along a longitudinal axis at distal end 106, such that opening 108 exposes at least a portion of the lumen of catheter shaft 104, providing a field of view for circuit board 110 disposed therein. Opening 108 may be formed by cutting out a section of catheter shaft 104 during fabrication of introducer device 102. Circuit board 110 may be flexible or rigid, and has array of sensors 112 disposed thereon. Preferably, array of sensors 112 are infrared sensors. Expandable structure 114 is formed of transmissive material, e.g., infrared transmissive foil, and shaped and sized to be disposed on distal end 106 of catheter shaft 104 to form a "viewing window" for array of sensors 112. In one embodiment, array of sensors 112 measures infrared radiation emitted by the intracavitary tissue adjacent to introducer device 102 through opening 108 of catheter shaft 104 and expandable structure 114.

Circuit board 110 may be slidably inserted into a lumen of catheter shaft 104 along rails such that array of sensors 112 is exposed from within catheter shaft 104 creating a field of view through opening 108. The rails may be rotatable such that circuit board 110 and array of sensors 112 may be rotationally positioned about the longitudinal axis of catheter shaft 104 to face the correct direction, e.g., toward the heart, to achieve the desired field of view. Preferably, circuit board 110 is rotatable such that array of sensors 112 remains exposed in opening 108 in the rotation range permitted by the rails, while providing additional viewing angles. For example, array of sensors 112 may be disposed within opening 108 of catheter shaft 104 to create a field of view having a predetermined angle, e.g., less than 180°, less than 150°, less than 120°, or less than 90°. Accordingly, circuit board 110 housing array of sensors 112 may be rotatable to adjust the angle of the field of view to a second, different predetermined angle, e.g., greater or less than the first predetermined angle. The rails may be rotated manually or may be coupled to a motor such that the rails may be rotated by the motor operated by the clinician. For example, the rails may be rotated by any amount up to 360 degrees.

In one embodiment, circuit board 110 may be fixed within catheter shaft 104. For example, stiffening wires made of a biocompatible material, e.g., stainless steel or nitinol, may be inserted through catheter shaft 104 to prevent circuit board 110 from moving from a desired viewing position, e.g., facing toward the heart, as described in further detail below.

In one embodiment, circuit board 110 may be reusable whereas catheter shaft 104 is disposable. For example, the more expensive circuit board having array of sensors 112 disposed thereon may be removably inserted into disposable catheter shaft 104 when used by the patient's clinician for measuring and monitoring purposes. At the end of the measurement and monitoring procedure, the disposable catheter shaft, the portion of introducer device 102 which contacts the patient's bodily lumen, may be discarded and circuit board 110 may be inserted into a new disposable catheter shaft for use with another patient, or the same patient at a later time.

Expandable structure 114 may be made of an infrared transmissive material, e.g., a thin film polymer having a thickness in the range of 5 micron to 1 mm. In addition, the infrared transmissive material may have transparency in the relevant wavelength range between 1 to 30 microns, or 4 to 16 microns, or 10 to 15 microns. For applications not requiring an optimal sensitivity or not needing a rapid detection, materials with less specific infrared transmissivity may be used for, e.g., their more suitable mechanical or physical properties. The space between array of sensors 112 and expandable structure 114 may be at least partially created by cutting out a section of distal end 106 of catheter shaft 104 to create opening 108. In one embodiment, catheter shaft 104 may include a glue lumen and a plurality of holes extending from the glue lumen to an external wall of catheter shaft 104 such that a glue, e.g., adhesive material, may be inserted within the glue lumen to affix catheter shaft 104 to expandable structure 114, as described in further detail below.

As shown in FIG. 1A, expandable structure 114 may be an inflatable bladder formed of infrared transmissive material. In an inflated state, the bladder may have an ovoid shape or an oval cross section to conform to the inside of a body lumen, e.g., esophagus. Preferably, expandable structure 114 is formed of a compliant or semi-compliant material. The bladder may be filled with air or a dry gas, thereby providing space in front of, or surrounding array of sensors 112, such that array of sensors 112 may see through the air or gas, creating a field of view of the adjacent intracavitary tissue so that array of sensors 112 may measure the tissue temperature directly. Specifically, array of sensors 112 may detect the temperature, e.g., infrared radiation, emitted from the intracavitary tissue through expandable structure 114, and through the air or gas in the space between array of sensors 112 and expandable structure 114. For example, the gas may be $CO_2$, Ar, He, or any other suitable gas selected based on the required infrared detection specificity and/or sensitivity. Alternatively, when there are no specific clinical requirements, air is preferably used. In addition, upon inflation, the inflatable bladder may provide an optimal viewing distance, e.g., 2 to 8 mm, between array of sensors 112 and the intracavitary tissue to be measured and monitored. As will be understood by a person having ordinary skill in the art, expandable structure 114 may be inflated via, e.g., a syringe pump, coupled to a proximal end of catheter shaft 104.

Software-based monitoring system 116 is installed and runs on a computer, and is used by the patient's clinician to monitor the measured temperature of the intracavitary tissue and/or to control functioning of introducer device 102. Preferably, the computer is electrically coupled to circuit board 110 and, thereby, to array of sensors 112. The computer may be a conventional computer such as a desktop, laptop, tablet, smartphone, mobile device, LCD display, or the like or may be an application specific computer customized for use with introducer device 102. For example, the computer may include a customized housing having a display for displaying the measured temperature of the intracavitary tissue and a fluid source in fluid communication with expandable structure 114 to expand, e.g., inflate, expandable structure 114, and may permit the clinician to activate expansion and/or a monitoring session. Introducer device 102 may be coupled, either wirelessly or using a cable, to the computer such that software-based monitoring system 116 may receive data indicative of the temperature of the intracavitary tissue. Software-based monitoring system 116 may be non-transitory computer readable media having instructions stored thereon that, when executed by a processor operatively coupled to circuit board 110, cause a graphical user interface to display and log internally information indicative of temperature of the intracavitary tissue based on signals received from array of infrared sensors 112. The instructions stored on software-based monitoring system 116, when executed by the processor, may also cause the graphical user interface to trigger an alarm if the generated signal indicative of temperature of the intracavitary tissue exceeds a predetermined threshold. Such an alarm allows the patient's clinician to cease or adjust application of thermal energy, e.g., RF ablation, to a nearby target tissue.

Figure 1B:
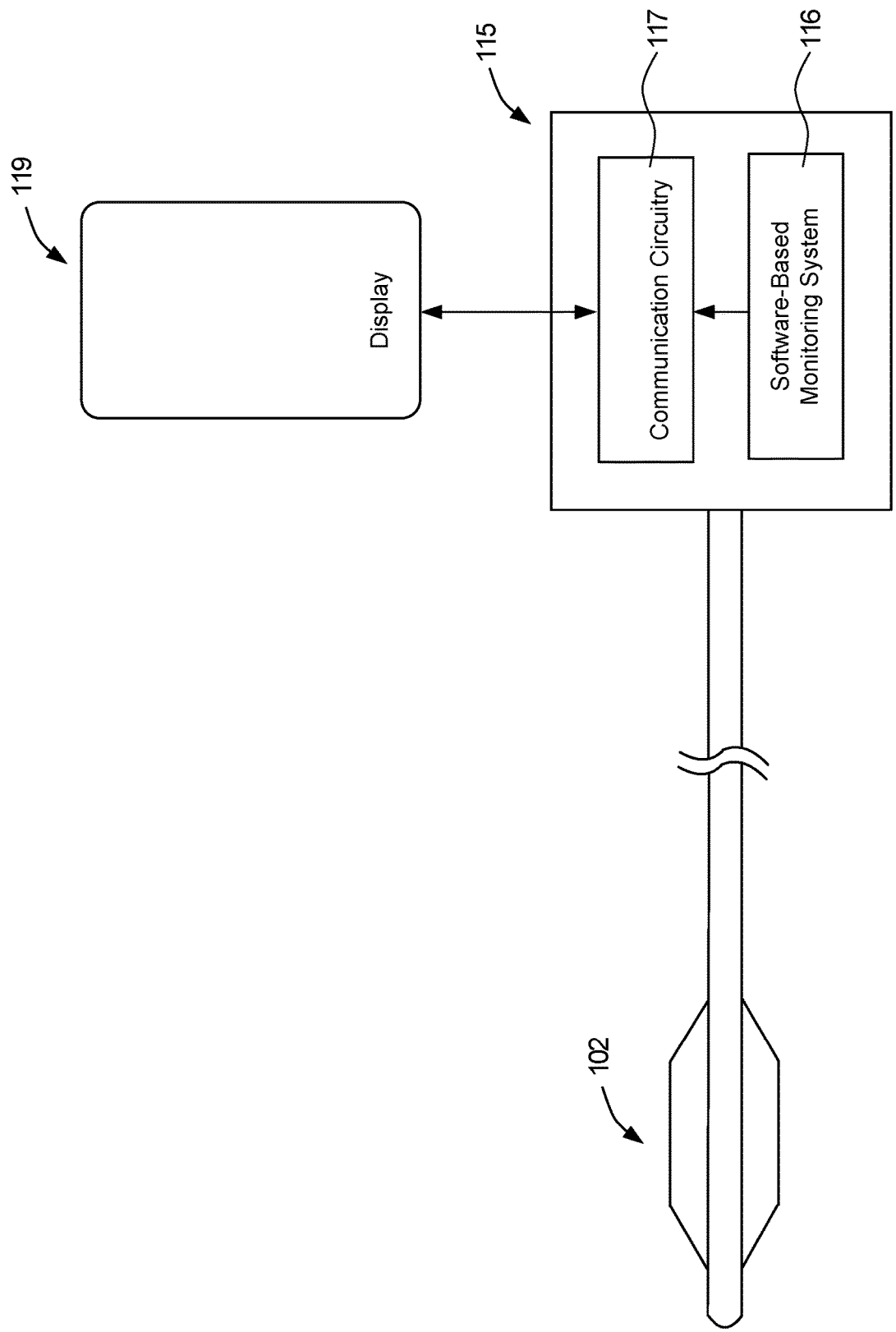
FIG. 1B is a schematic view of an alternative embodiment of a system constructed in accordance with the principles of the present invention.

As shown in FIG. 1B, the computer, e.g., data acquisition box 115, may include communication circuitry 117, e.g., cellular (e.g., 3G, LTE, etc.) chipset, IEEE 802.11 (e.g., WiFi) chipset, Bluetooth chipset, or the like, for wired and/or wireless communication with additional computers, e.g., display 119. Display 119 may include, for example, a desktop, laptop, tablet, smartphone, mobile device, LCD display, or the like. In this manner, software-based monitoring system 116 may cause data collected at data acquisition box 115 from introducer device 102 to be transmitted remotely to display 119 for, for example, display, analysis, and/or storage.

Figure 2:
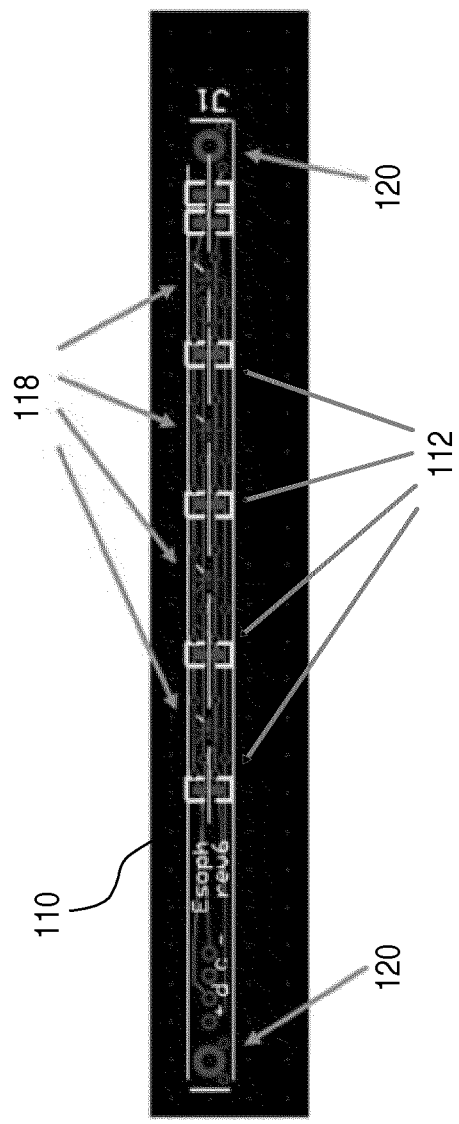
FIG. 2 illustrates the circuit board of FIG. 1A.

Referring now to FIG. 2, a detailed description of circuit board 110 is provided. As described above, circuit board 110 may be flexible or rigid and has array of sensors 112 mounted thereon. A flexible circuit board may be either the full length of catheter shaft 104, going from a connector at the proximal end of catheter shaft 104 to the distal end of catheter shaft 104, or the flexible circuit board may be long enough to hold array of sensors 112 such that array of sensors 112 are connected to discrete wires to communicate signals from the flexible circuit board to the connector. In one embodiment, circuit board 110 is slightly longer than opening 108. The sensors of array of sensors 112 may be spaced apart along circuit board 112 in a manner so as to maximize the field of view of the surface area of the intracavitary tissue desired to be measured and monitored. As will be understood by one of ordinary skill in the art, array of sensors 112 may be selected from infrared sensitive photodiodes, infrared sensitive transistors, infrared sensitive photocells, and infrared sensitive thermopiles. Preferably, array of sensors 112 includes infrared sensitive thermopiles that generate an output voltage proportional to a local temperature difference of the intracavitary tissue. As will also be understood by one of ordinary skill in the art, array of sensors 112 may have more or less than four infrared sensors, e.g., depending on the surface area of the intracavitary tissue desired to be measured and monitored.

Each sensor of array of sensors 112 may include integrated circuitry 118. In one embodiment, array of sensors 112 detects extremely small amounts of energy from the infrared radiation input and filters and amplifies the detected energy into a meaningful and useful value via circuitry 118. Circuitry 118 may conduct signal processing which varies from a simple filter/amplifier that outputs an analog value, to a more complicated processing system involving circuit temperature compensation and conversion to other formats such as a digital output. For example, circuitry 118 may amplify the signal, filter the signal, perform compensation for local actual temperature of the array of infrared sensors irrespective of the infrared input, and convert the signal to a digital serial stream for convenient use by the clinician's computer. Circuitry 118 may be electrically coupled to the clinician's computer such that software-based monitoring system 116 may receive data indicative of the temperature of the intracavitary tissue directly from array of sensors 112.

Circuit board 110 may include orientation markers 120. For example, orientation markers 120 may be etched into circuit board 110 and viewable under fluoroscopy. As shown in FIG. 2, orientation markers 120 may comprise a large circle and two small circles. Alternatively, orientation markers 120 may comprise any pattern of shapers and/or markers easily identifiable under fluoroscopy by the patient's clinician to ensure proper orientation of circuit board 110.

Referring now to FIG. 3A, an alternative exemplary embodiment of introducer device 100 is provided. Introducer device 102' is constructed similarly to introducer device 102 of FIG. 1A, wherein like components are identified by like-primed reference numbers. Thus, for example, catheter shaft 104' in FIG. 3A corresponds to catheter shaft 104 of FIG. 1A, circuit board 110' in FIG. 3A corresponds to circuit board 110 of FIG. 1A, array of sensors 112' in FIG. 3A corresponds to array of sensors 112 of FIG. 1A, etc. As shown in FIG. 3A, expandable structure 115 may be an unrestrained pillow shaped inflatable bladder having a flat width with catheter shaft 104' and array of sensors 112' disposed in opening 108' along catheter shaft 104'. Specifically, the unrestrained pillow shaped inflatable bladder may completely encapsulate catheter shaft 104' including opening 108' to thereby provide a field of view of the intracavitary tissue to array of sensors 112'. In one embodiment, catheter shaft 104' may include a glue lumen and a plurality of holes extending from the glue lumen to an external wall of catheter shaft 104' such that a glue, e.g., adhesive material, may be inserted within the glue lumen to affix catheter shaft 104' to one side of the unrestrained pillow shaped inflatable bladder, e.g., the side adjacent the dorsal side of the esophagus. The unrestrained pillow shaped inflatable bladder may have fixed dimensions upon inflation with an air or gas as described above. Alternatively, the unrestrained pillow shaped inflatable bladder may have dimensions that change upon inflation based on infusion pressure of the air or gas within the bladder.

Opening 108' provides array of sensors 112' with field of view FOV by exposing at least a portion of array of sensors 112', such that the field of view depends on the geometry of opening 108'. For example, a wider opening provides a wider field of view of a larger surface area of the target intracavitary tissue, and a narrow opening provides a narrower field of view of a smaller surface area of the target intracavitary tissue. As described above, circuit board 110' along with array of sensors 112' may be rotated via rotatable rails within the lumen of catheter shaft 104', thereby changing the field of view. The rotation of array of sensors 112' allows proper orientation in a desired direction toward the target portion of the intracavitary tissue to be measured and monitored.

As shown in FIG. 3A, the unrestrained pillow shaped inflatable bladder may be inflated such that it has an ovoid shape or an oval cross section to conform to the inside of a body lumen, e.g., esophagus. The unrestrained pillow shaped inflatable bladder may provide an optimal viewing distance, e.g., 2 to 8 mm, between array of sensors 112' and the intracavitary tissue to be measured and monitored. The inflation of the unrestrained bladder may be pressure controlled such that the bladder stops inflating when it conforms to the body lumen or cavity. For application in an esophagus, the bladder's conformity to the naturally oval shape of the esophagus facilitates the orientation of introducer device 102' and array of sensors 112' with the intracavitary tissue to be measured and monitored. In addition, the oval shape of the inflated bladder may prevent the esophagus from being pushed out of its normal anatomical position in the patient's body. For example, the esophagus would not be pushed toward the heart during intracavitary temperature measurement and monitoring, thereby avoiding the risk of reducing the tissue-thickness between the esophagus and the heart's atria which would increase the risk of thermal damage to the esophagus during RF ablation of the atrial tissue. In one embodiment, the unrestrained inflatable bladder may be shaped so that when it is inflated, the bladder may cause the esophagus to pull away from the heart. As will be understood by one of ordinary skill in the art, the unrestrained inflated bladder may have other shapes including a spherical shape, a cylindrical shape, or a dumbbell shape depending on the application.

Referring to now to FIG. 3B, introducer device 102" is constructed similarly to introducer device 102 of FIG. 1A, wherein like components are identified by like-primed reference numbers. Thus, for example, catheter shaft 104" in FIG. 3B corresponds to catheter shaft 104 of FIG. 1A, circuit board 110" in FIG. 3B corresponds to circuit board 110 of FIG. 1A, array of sensors 112" in FIG. 3B corresponds to array of sensors 112 of FIG. 1A, etc. As shown in FIG. 3B, expandable structure 117 may be a restrained pillow shaped inflatable bladder. The restrained bladder of FIG. 3B may operate in a similar manner to the unrestrained bladder of FIG. 3A. For example, the inflation of the restrained bladder may be pressure controlled, the restrained bladder may be inflated with an air or a dry gas, the restrained bladder may provide an optimal viewing distance, e.g., 2 to 8 mm, between array of sensors 112" and the intracavitary tissue to be measured and monitored, etc.

In addition, the restrained pillow shaped inflatable bladder may be shaped similar to the unrestrained bladder of FIG. 3A on one side of the restrained bladder, e.g., the side adjacent the ventral side of the esophagus facing the heart, whereas the other side, e.g., the side adjacent the dorsal side of the esophagus, is restrained, thereby creating communication channel 122 running along the longitudinal axis of catheter shaft 104" between the proximal end and the distal end of expandable structure 117. Communication channel 122 may be formed as a recess between catheter shaft 104" and expandable structure 117. For example, expandable structure 117 may not completely encapsulate catheter shaft 104", leaving the bottom portion of catheter shaft 104" exposed to engage with the intracavitary tissue, e.g., the dorsal side of the esophagus as shown in FIG. 3C. Specifically, expandable structure 117 may be disposed on catheter shaft 104" such that it encapsulates opening 108" to provide a field of view of the intracavitary tissue, but does not encapsulate the bottom portion of catheter shaft 104". As such, expandable structure 117 conforms with the body lumen in front of opening 108" and curves inward toward catheter shaft 104" on opposite sides of catheter shaft 104", thereby creating communication channel 122. Communication channel 122 may facilitate the displacement of air and liquids on the dorsal side of the body lumen or cavity, e.g., esophagus, while maintaining full continuous temperature measurement on the ventral side of the body lumen or cavity. For example, for applications in esophagus E as shown in FIG. 3C, communication channel 122 may be adjacent to the dorsal side of the esophagus, whereas array of sensors 112" have a field of view on the ventral side of the esophagus facing the heart. In addition, as will be understood by one of ordinary skill in the art, the shape of the restrained bladder is not limited to a pillow shape.

The restrained bladder may include reinforcement features, e.g., wires, straps, flaps, etc., mounted on or behind the backside of the restrained bladder adjacent to the exposed portion of catheter shaft 104" to improve mechanical stability of introducer device 102", e.g., push-ability, catheter shaft advancement, rotational positioning, etc. The reinforcement features may assist the formation of communication channel 122. As will be understood by one of ordinary skill in the art, the present invention is not limited to application in the esophagus and may be used for, e.g., measurement of the colon surface during prostate surgery and/or ablation.

Referring now to FIGS. 4A and 4B, another embodiment of introducer device 102 is described. Introducer device 102''' is constructed similarly to introducer device 102 of FIG. 1A, wherein like components are identified by like-primed reference numbers. Thus, for example, catheter shaft 104''' in FIGS. 4A and 4B corresponds to catheter shaft 104 of FIG. 1A, circuit board 110''' in FIGS. 4A and 4B corresponds to circuit board 110 of FIG. 1A, array of sensors 112''' in FIGS. 4A and 4B corresponds to array of sensors 112 of FIG. 1A, etc. As will be observed by comparing FIGS. 4A and 4B with previous embodiments, introducer device 102''' may include transmissive material 124, e.g., infrared transmissive foil, that creates the "viewing window" for array of sensors 112''' by being coupled to catheter shaft 104''' over opening 108''' rather than an expandable structure. Transmissive material 124 encloses the space between array of sensors 112''' and transmissive material 124 and may be made of an infrared transmissive material, e.g., a thin film polymer having a thickness in the range of 5 micron to 1 mm. In addition, infrared transmissive material 124 may have transparency in the relevant wavelength range between 1 to 30 microns, 4 to 16 microns, or 10 to 15 microns. As described above, for applications not requiring an optimal sensitivity or not needing a rapid detection, materials with less specific infrared transmissivity may be used for, e.g., their more suitable mechanical or physical properties. The space between array of sensors 112''' and transmissive material 124 may be at least partially created by cutting out a section of distal end 106''' of catheter shaft 104''' to create opening 108''', and covering opening 108''' by sealing or gluing transmissive material 124 to the edges of opening 108'''.

Referring now to FIG. 5A, another embodiment of introducer device 102 is described. Introducer device 502 is constructed similarly to introducer device 102''' of FIG. 4A. For example, circuit board 510 in FIG. 5A corresponds to circuit board 110''' in FIG. 4A, array of sensors 512 in FIG. 5A corresponds to array of sensors 112''' in FIG. 4A, transmissive material 524 in FIG. 5A corresponds to transmissive material 124 in FIG. 4A, etc. As will be observed by comparing FIG. 5A with previous embodiments, catheter shaft 504 may include wire lumen 506 and glue lumen 516. A stiffening wire(s) made of, e.g., stainless steel or nitinol, may be inserted through lumen 506 of FIG. 5A to prevent circuit board 510 from moving after circuit board 510 has been positioned in its desired location, e.g., facing the ventral side of the esophagus. The stiffening wire(s) may also keep the orientation of circuit board 510 planar within catheter shaft 504. Alternatively or additionally, the stiffening wire(s) may be inserted within cavity 514 of catheter shaft 504.

Catheter shaft 504 may be encapsulated by an unrestrained pillow shaped inflatable bladder. Accordingly, glue lumen 516 of FIG. 5A may have holes 518 extending therefrom to the external wall of catheter shaft 504 along the longitudinal axis of catheter shaft 504, thereby connecting glue lumen 516 with the external wall of catheter shaft 504. Holes 518 may include a plurality of holes spaces apart along the longitudinal axis of catheter shaft 504 or may be one single elongated hole. As such, a glue, e.g., adhesive material, may be inserted within glue lumen 516 of FIG. 5A, and exit via holes 518, such that catheter shaft 504 may be affixed to one side of the unrestrained pillow shaped inflatable bladder, e.g., the side adjacent the dorsal side of the esophagus.

Referring now to FIG. 5B, another embodiment of introducer device 502 is described. Introducer device 502' is constructed similarly to introducer device 502 of FIG. 5A, wherein like components are identified by like-primed reference numbers. Thus, for example, wire lumen 506' in FIG. 5B corresponds to wire lumen 506 in FIG. 5A, circuit board 510' in FIG. 5B corresponds to circuit board 510 in FIG. 5A, array of sensors 512' in FIG. 5B corresponds to array of sensors 512 in FIG. 5A, glue lumen 516' in FIG. 5B corresponds to glue lumen 516 in FIG. 5A, holes 518' in FIG. 5B corresponds to holes 518 in FIG. 5A, transmissive material 524' in FIG. 5B corresponds to transmissive material 524 in FIG. 5A, etc. Accordingly, catheter shaft 504' may be encapsulated by an unrestrained pillow shaped inflatable bladder such that a glue may be inserted within glue lumen 516' of FIG. 5B, and exit via holes 518', such that catheter shaft 504' may be affixed to one side of the unrestrained pillow shaped inflatable bladder, e.g., the side adjacent the dorsal side of the esophagus.

As will be observed by comparing FIG. 5B with FIG. 5A, wire lumen 506' may be positioned below a center line of catheter 502', e.g., toward the dorsal side of the esophagus. Accordingly, array of electrodes 512' may be spaced farther apart from transmissive material 524' when compared with array of electrodes 512 and transmissive material 524 of FIG. 5A, such that opening 508' may be larger than opening 508.

Referring now to FIGS. 6A and 6B, an alternative embodiment of introducer device 602 is described. Introducer device 602 is constructed similarly to introducer device 102 of FIG. 1A, wherein like components are identified by like-primed reference numbers. Thus, for example, catheter shaft 604 in FIGS. 6A and 6B corresponds to catheter shaft 104 of FIG. 1A, opening 608 in FIGS. 6A and 6B corresponds to opening 108 of FIG. 1A, circuit board 610 in FIGS. 6A and 6B corresponds to circuit board 110 of FIG. 1A, etc. As shown in FIGS. 6A and 6B, introducer device 602 may have support members 624. Each support member 624 has end portions 626 and 630, and middle portion 628. End portions 626 and 630 of support members 624 are coupled to the ends of catheter shaft 604 adjacent to the proximal and distal ends of opening 608 such that middle portion 628 is parallel to the longitudinal axis of catheter shaft 604 in a delivery state as shown in FIG. 6A, and curved outwardly away from catheter shaft 604 to engage the intracavitary tissue in a deployed state as shown in FIG. 6B. As middle portion 628 of support members 624 curves outwardly away from catheter shaft 604 as introducer device 602 transitions from the delivery state to the deployed state, end portion 630 causes the portion of catheter shaft 604 coupled to end portion 630 to move over circuit board 610 toward end portion 626. In this embodiment, a transmissive material covering opening 608 may create a field of view for the array of sensors. As will be understood by one of ordinary skill in the art, introducer device 602 may have more or less than two support members 624. For example, introducer device 602 may have three or more support members 624.

Figure 7:
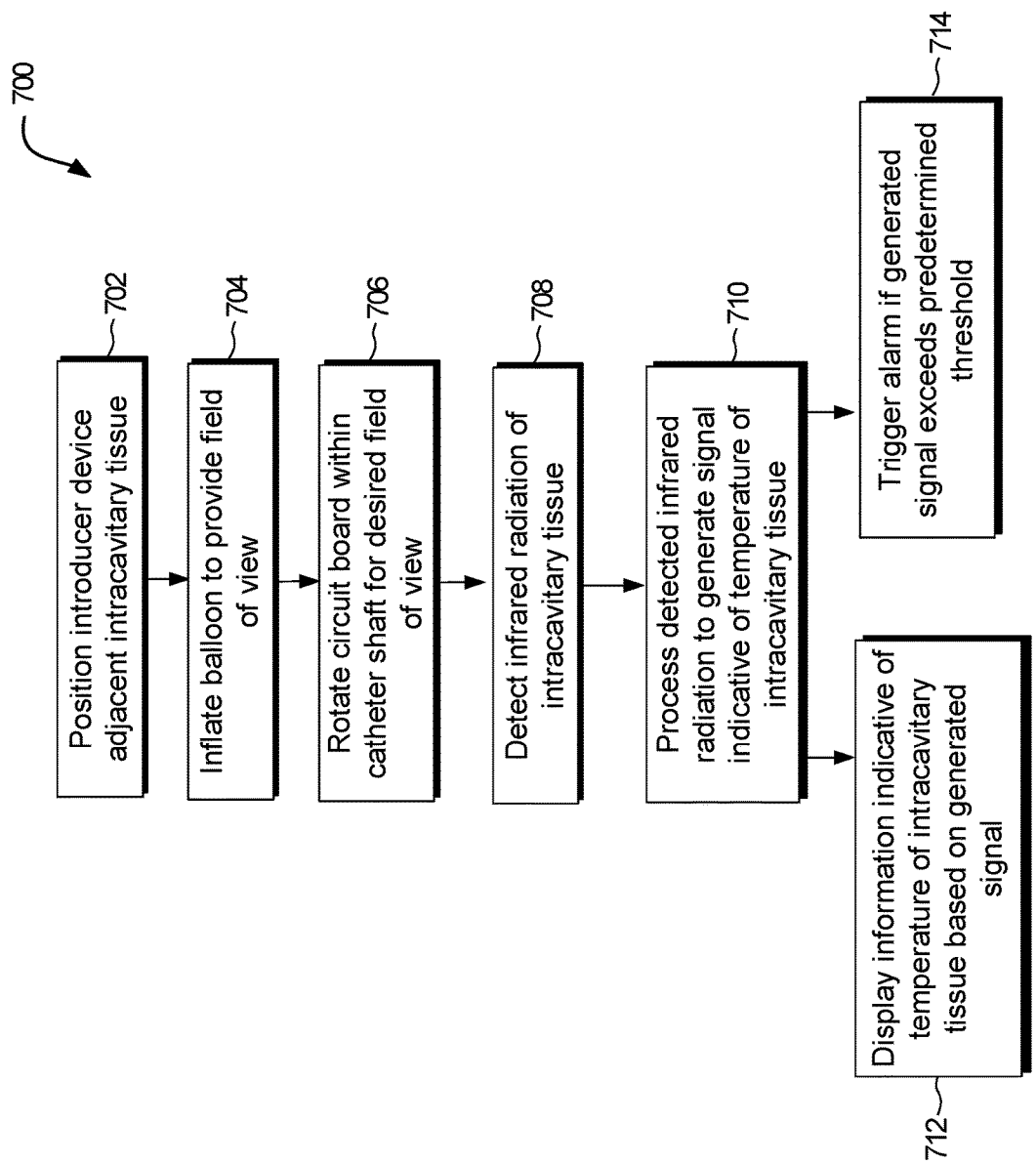
FIG. 7 illustrates an exemplary method for using the system of FIG. 1A to measure and monitor intracavitary temperature in accordance with the principles of the present invention.

Referring now to FIG. 7, exemplary method 700 for using the system of FIG. 1A to measure and monitor intracavitary temperature in accordance with the principles of the present invention is provided. At 702, the clinician positions introducer device 102 adjacent to an intracavitary tissue to be measured and monitored, e.g., esophageal tissue, such that opening 108 of catheter shaft 104 is oriented toward the intracavitary tissue. As described above, circuit board 110 may be slidably inserted into the lumen of catheter shaft 104 along rotatable rails. As such, circuit board 110 may be slidably inserted into the lumen of catheter shaft 104 after introducer device 102 has been positioned adjacent to the intracavitary tissue. Alternatively, circuit board 110 may be slidably inserted and fixed within catheter shaft 104 prior to the positioning of introducer device 102 adjacent to the intracavitary tissue.

At 704, the clinician inflates expandable structure 114, e.g., unrestrained or restrained pillow shaped inflatable bladder described above, to provide array of sensors 112 a field of view of the portion of the intracavitary tissue to be measured and monitored through opening 108, transmissive expandable structure 114, and the air or gas used to inflate expandable structure 114 therebetween. In addition, inflating expandable structure 114 provides an optimal viewing distance between array of sensors 112 and the intracavitary tissue.

At 706, the clinician optionally rotates circuit board 110 within the lumen of catheter shaft 104 to achieve a desired field of view of the portion of the intracavitary tissue to be measured an monitored. The clinician may rotate circuit board 110 within a range of 360 degrees about the longitudinal axis of catheter shaft 104 in either direction, e.g., clockwise or counter-clockwise. The physician may rotate circuit board 110 manually or via a motor coupled to the rails. In addition, the clinician may adjust circuit board 110 along the longitudinal axis of catheter shaft 104 by sliding circuit board 110 along the rails to assist in achieving the desired field of view of the intracavitary tissue. In an embodiment where the catheter shaft includes one or more wire lumens, a stiffening wire may be inserted within the one or more wire lumens to prevent the circuit board from moving after being positioned in the desired location.

At 708, clinician instructs array of sensors 112 to detect the infrared radiation emitting from the intracavitary tissue. At 710, integrated circuitry 118 of each infrared sensor of array of sensors 112 processes the detected infrared radiation to generate a signal indicative of temperature of the intracavitary tissue. Processing the detected infrared radiation may include amplifying the signal, filtering the signal, performing compensation for local actual temperature of the one or more infrared sensors, and converting the signal to a digital serial stream for convenient use by the clinician's computer. The generate signal is then received by the clinician's computer either wirelessly or by a cable coupled to both circuit board 110 and the clinician's computer.

At 712, the information indicative of temperature of the intracavitary tissue based on the generated signal may be displayed on a graphical user interface. In addition, at 714, an alarm may be triggered on the graphical user interface to alert the clinician or the patient if the generated signal indicative of temperature of the intracavitary tissue exceeds a predetermined threshold. As a result, the clinician may adjust operations, e.g., reduce RF ablation of atrial tissue so as to avoid injuring the intracavitary tissue, thereby preventing, for example, esophageal injury and/or atrio-esophageal fistula.

Referring now to FIGS. 8A-D, an exemplary method for manufacturing an expandable structure, e.g., a bladder, is described. As shown in FIG. 8A, tube 800 may be provided for manufacturing the expandable structure. Tube 800 may be formed of a thin, flexible, infrared-transmissive material, e.g., high-density polyethylene (HDPE) or other materials having similar properties, such that tube 800 may be expanded and contracted. Preferably, tube 800 is formed of a compliant or semi-compliant material. Tube 800 is shaped and sized to at least partially encapsulate an introducer device as described above, and may have a lumen extending therethrough having, e.g., a circular cross-sectional area.

As shown in FIG. 8B, the expandable structure is stamped out of tube 800 by sealing tube 800 via a sealing machine. For example, sealing of tube 800 may be achieved by applying a heating plate on portion 802 of tube 800. As will be understood by a person having ordinary skill in the art, any commercially available sealing machine may be used to seal tube 800. The heating plate will apply heat to portion 802 to form mid-portion 808, conical portion 804, and straight end portion 806 of the expandable structure, such that the lumen of tube 800 extends continuously through mid-portion 808, conical portion 804, and end portion 806. As shown in FIG. 8B, heat may be applied by a heating plate to an upper portion and a lower portion of portion 802 of tube 800, or heat may be applied circumferentially around portion 802. As heat is applied to portion 802, the cross-sectional area of tube 800 at mid-portion 808, changes from a first cross-sectional shape, e.g., a circular cross-sectional shape, to a second cross-sectional shape, e.g., an oval cross-sectional shape. Advantageously, heat applied to conical portion 804 and end portion 806 causes mid-portion 808 to change cross-sectional shape from the first shape to the second shape without the need to apply the heating plate to mid-portion 808. The cross-sectional shape of end portion 806 may be circular or oval in shape, and is preferably sized and shaped to receive a catheter shaft of the introducer device described herein. Sealed tube 800 having mid-portion 808, conical portion 804, and end portion 806 is illustrated in FIG. 8C.

As shown in FIG. 8D, the excess materials are cut off end portion 806 of sealed tube 800 to form one end of the expandable structure having mid-portion 808, conical portion 804, and remaining end portion 806. The above described method steps may be applied to another portion of tube 800 simultaneously or at a different time, a predetermined distance from end portion 806 such that mid-portion 808 has a desirable length for the applications described herein, thereby forming the other end of the expandable structure to form a complete expandable structure. FIG. 8D shows forming conical portion 804 and end portion 806 of two separate expandable members. The expandable members may have a shape such as that shown in FIG. 3A.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A system for intracavitary tissue measurement and monitoring, the system comprising:
    an introducer device configured to be positioned adjacent to an intracavitary tissue, the introducer device comprising:
        a catheter shaft having a distal end, a longitudinal axis, and a lumen extending therethrough, the catheter shaft having an opening at the distal end along the longitudinal axis such that at least a portion of the lumen is exposed;
        a circuit board having an array of infrared sensors disposed thereon, the circuit board disposed within the lumen of the catheter shaft at least partially in the opening at the distal end, the array of infrared sensors each having circuitry configured to generate a signal indicative of temperature of the intracavitary tissue; and
        an expandable structure formed from an infrared transmissive material and disposed along the longitudinal axis on the distal end of the catheter shaft to surround the array of infrared sensors and to provide a field of view through the opening such that the opening is in fluid communication with an interior of the expandable structure; and
    a non-transitory computer readable media having instructions stored thereon, wherein the instructions, when executed by a processor operatively coupled to the circuit board, cause a graphical user interface to display information indicative of temperature of the intracavitary tissue based on the signal from the array of infrared sensors.

2. The system of claim 1, wherein the introducer device is configured to be positioned adjacent esophageal tissue.

3. The system of claim 1, wherein the catheter shaft comprises one or more support members, each of the one or more support members having end portions coupled to the catheter shaft and a middle portion configured to be positioned parallel to the longitudinal axis of the catheter shaft in a delivery state, and curved outwardly away from the catheter shaft to engage the intracavitary tissue in a deployed state.

4. The system of claim 1, wherein the circuit board is flexible.

5. The system of claim 1, wherein the circuit board is further configured to be fixed within the lumen of the catheter shaft.

6. The system of claim 1, wherein the array of infrared sensors comprises at least one of infrared sensitive photodiodes, infrared sensitive transistors, infrared sensitive photocells, or infrared sensitive thermopiles.

7. The system of claim 1, wherein the circuitry is configured to generate the signal indicative of temperature of the intracavitary tissue by amplifying the signal, filtering the signal, performing compensation for temperature of the array of infrared sensors, and converting the signal to a digital serial stream.

8. The system of claim 1, wherein the circuit board is configured to be slidably inserted within the lumen of the catheter shaft, the circuit board further configured to be rotated within the lumen of the catheter shaft to enhance the field of view.

9. The system of claim 1, wherein the circuit board further comprises one or more orientation markers configured to be viewable under fluoroscopy.

10. The system of claim 1, wherein the expandable structure comprises a thin polymer having a thickness within a range between 5 micron to 1 mm, and wherein the infrared transmissive material of the expandable structure has a transparency comprising a wavelength within a range between 4 to 16 microns.

11. The system of claim 1, wherein the expandable structure is an inflatable bladder, the inflatable bladder configured to orient the introducer device and to provide an optimal viewing distance between the circuit board and the intracavitary tissue within a range between 2 to 8 mm.

12. The system of claim 11, wherein the inflatable bladder is inflated with an air or gas selected based on desired infrared detection specificity and sensitivity, the gas comprising at least one of $CO_2$, Ar, or He.

13. The system of claim 11, wherein the inflatable bladder comprises a pillow shape having an ovoid shape, a spherical shape, a cylindrical shape, or a dumbbell shape.

14. The system of claim 11, wherein the inflatable bladder is configured to be selectively restrained upon inflation such that the inflatable bladder is asymmetrically disposed on the catheter shaft to provide a communication channel between the inflatable bladder and the intracavitary tissue, and wherein the inflatable bladder comprises a reinforcement feature configured to reinforce the communication channel between the inflatable bladder and the intracavitary tissue, the reinforcement feature comprising at least one of wires, straps, or flaps.

15. The system of claim 11, wherein the inflatable bladder is configured to inflate in a pressure controlled manner within an esophagus such that the esophagus is not moved from its normal anatomical position relative to a heart.

16. The system of claim 1, wherein the instructions stored on the non-transitory computer readable media, when executed by the processor, further causes the graphical user interface to trigger an alarm if the generated signal indicative of temperature of the intracavitary tissue exceeds a predetermined threshold.

17. A method for measuring and monitoring intracavitary tissue temperature, the method comprising:
  selecting an introducer device comprising a catheter shaft having a lumen and an opening, a circuit board having one or more infrared sensors disposed thereon and circuitry coupled to the one or more infrared sensors, and an inflatable bladder surrounding the one or more infrared sensors such that the opening is in fluid communication with an interior of the inflatable bladder;
  positioning the introducer device adjacent to an intracavitary tissue such that the opening of the catheter shaft is oriented toward the intracavitary tissue;
  inflating the inflatable bladder to provide a field of view through the opening and the inflatable bladder, and an optimal viewing distance between the one or more infrared sensors and the intracavitary tissue;
  rotating the circuit board within the lumen of the catheter shaft to achieve a desired field of view;
  detecting infrared radiation of the intracavitary tissue from the one or more infrared sensors;
  processing the detected infrared radiation via the circuitry to generate a signal indicative of temperature of the intracavitary tissue; and
  displaying information indicative of temperature of the intracavitary tissue based on the generated signal on a graphical user interface.

18. The method of claim 17, further comprising inserting the circuit board within the lumen of the catheter shaft after the introducer device is positioned adjacent to the intracavitary tissue.

19. The method of claim 17, wherein processing the detected infrared radiation via the circuitry to generate a signal indicative of temperature of the intracavitary tissue comprises:
  amplifying the signal;
  filtering the signal;
  performing compensation for temperature of the one or more infrared sensors; and
  converting the signal to a digital serial stream.

20. The method of claim 17, further comprising triggering an alarm on the graphical user interface if the generated signal indicative of temperature of the intracavitary tissue exceeds a predetermined threshold.

* * * * *